United States Patent [19]

Cramer

[11] Patent Number: 4,800,890
[45] Date of Patent: Jan. 31, 1989

[54] STEERABLE GUIDE WIRE FOR CATHETERS

[76] Inventor: Bernhard M. Cramer, Heusnerstrasse 40, D-5600 Wuppertal 2, Fed. Rep. of Germany

[21] Appl. No.: 813,435

[22] Filed: Dec. 26, 1985

[30] Foreign Application Priority Data

Dec. 28, 1984 [DE]  Fed. Rep. of Germany ....... 3447642

[51] Int. Cl.$^4$ ............................................. A61B 6/00
[52] U.S. Cl. .................................... 128/657; 604/95; 604/170
[58] Field of Search ............... 128/657, 658, 772, 4–8, 128/343, 344; 604/95, 170, 109, 221, 222, 297, 334

[56] References Cited

U.S. PATENT DOCUMENTS

| | | | |
|---|---|---|---|
| 2,118,631 | 5/1938 | Wappler | 604/170 |
| 3,406,685 | 10/1968 | May | 604/170 |
| 3,452,740 | 7/1969 | Muller | 604/95 |
| 3,757,768 | 9/1973 | Kline | 128/657 |
| 3,906,938 | 9/1975 | Fleischhacker | 604/170 |
| 4,020,829 | 5/1977 | Willson et al. | 128/657 |
| 4,033,331 | 7/1977 | Guss et al. | 128/657 |
| 4,449,532 | 5/1984 | Storz | 128/20 |
| 4,456,017 | 6/1984 | Miles | 128/772 |
| 4,538,622 | 9/1985 | Samson et al. | 128/772 |
| 4,545,390 | 10/1985 | Leary | 128/657 |
| 4,554,929 | 11/1985 | Samson et al. | 128/657 |
| 4,582,181 | 4/1986 | Samson | 604/95 |

Primary Examiner—Max Hindenburg
Attorney, Agent, or Firm—Martin A. Farber

[57] ABSTRACT

In a steerable, flexible, torsionally-stable guide wire for medical catheters which is surrounded at its distal end region by a helically wound spring which protrudes beyond the end of the guide wire, an improved atraumatic guidance of the guide wire within particularly narrow passages is obtained in the manner that the guide wire is a continuously hollow metal tube (2) the outside diameter of the metal tube (2) is about 0.1 to 1.0 mm and preferably 0.2 to 0.5 mm at least in the distal end region (3), and at least the distal end region (3) of the metal tube (2) is cylindrical. In this way it is possible to apply contrast agent or therapeutic agent to the tip of the guide wire and advance it in this way under fluoroscopic control.

9 Claims, 6 Drawing Sheets

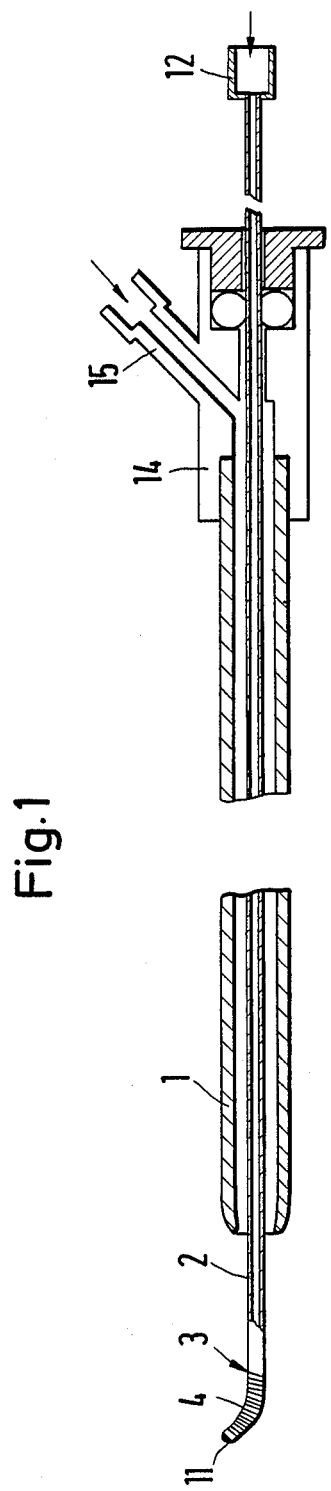

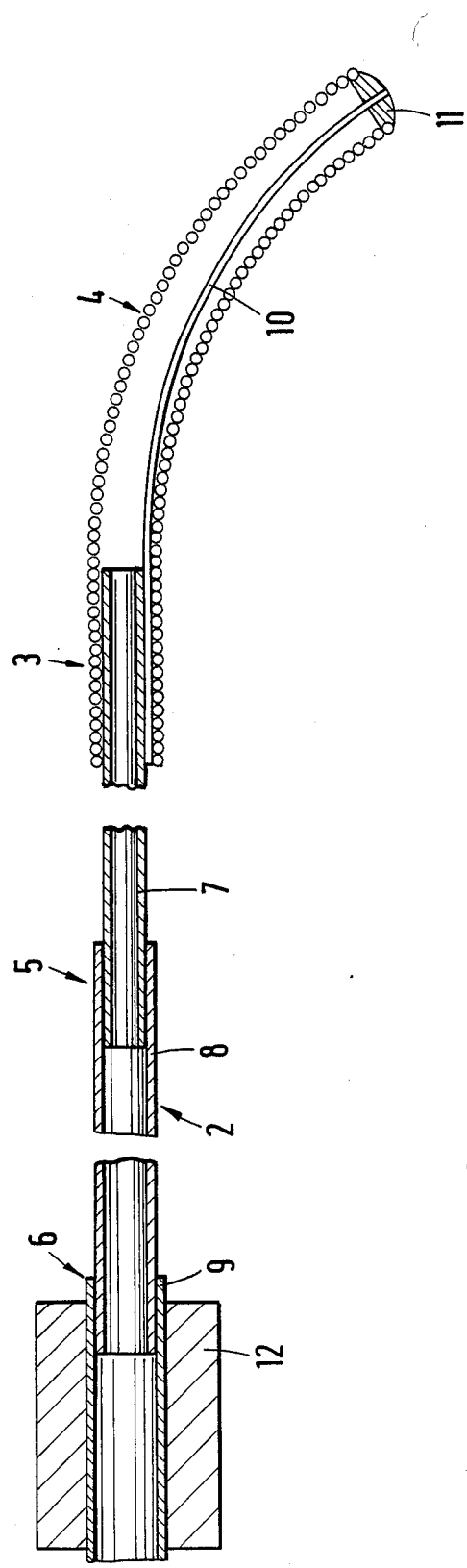
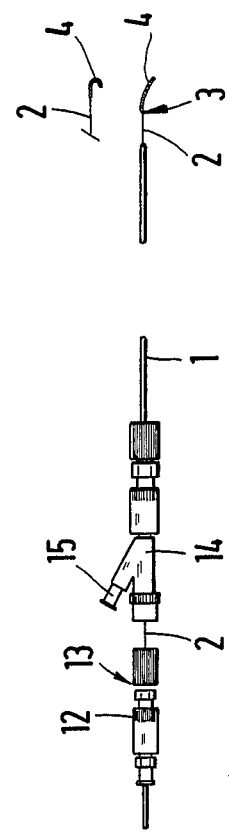

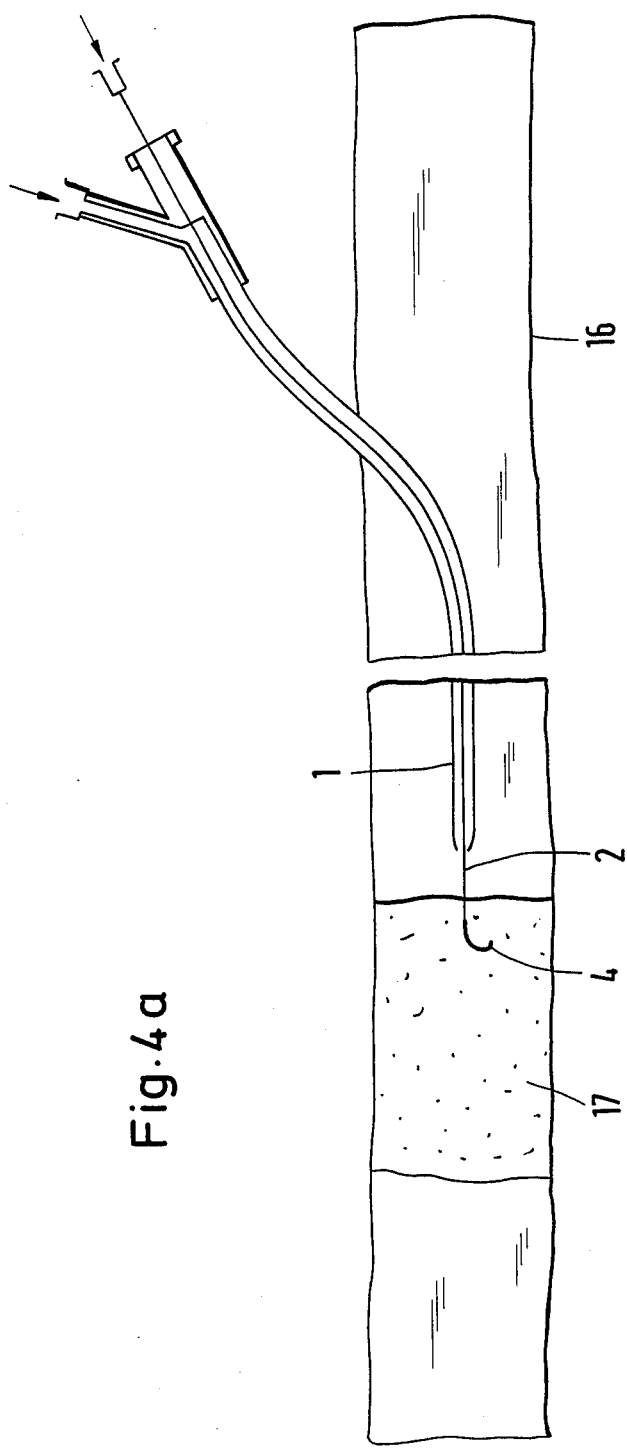

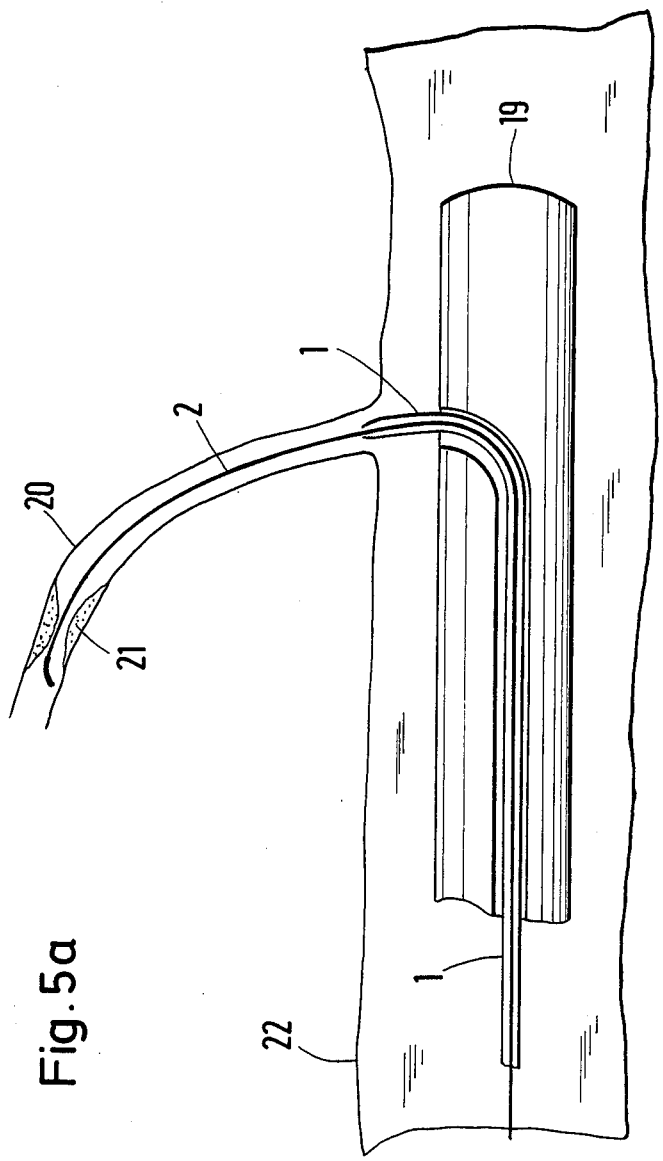

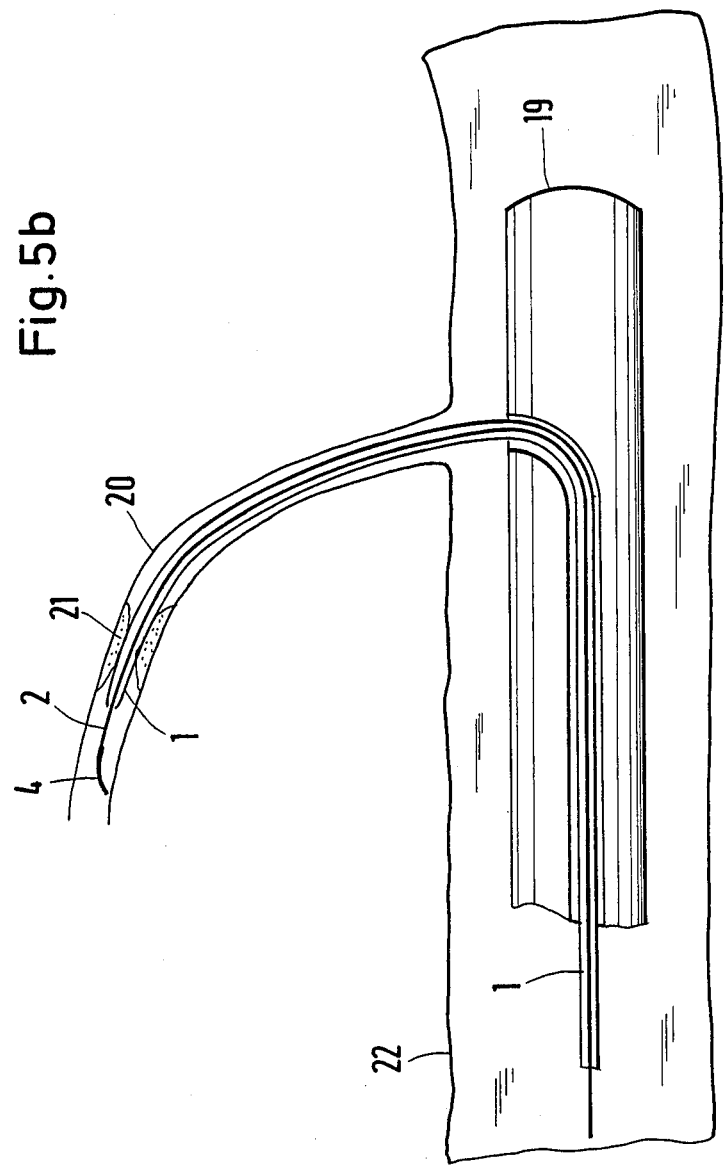

STEERABLE GUIDE WIRE FOR CATHETERS

BACKGROUND OF THE INVENTION

The invention relates to a guide wire in accordance with the preamble to Claim 1.

The catheters used in medical practice are flexible tubes, particularly of plastic, which are hollow throughout and can be introduced into cavities and canals of the human or animal body and serve to effect treatment within the body cavity or the canal or to make the body cavity or the canal visible by fluoroscopic or endoscopic methods. For this purpose, the catheters are introduced into the lumen in question. A therapeutic or contrast liquid can then be injected through the hollow of the catheter or a light guide can be introduced for endoscopic photographs or treatment with laser beam. For the avoidance of traumas and to assure sufficient flexibility, the material of the catheter is relatively soft and therefore can withstand only slight mechanical stresses. Accordingly, it is not possible to use such catheters to reach into fine branchings of the canal system, for instance of the blood vessels. Neither the torsional stability nor the required fineness of the catheter is sufficient for this.

In order to solve this problem, so-called guide wires have been developed whose outside diameters are between about 0.5 and 2 mm. Helically wound springs are provided at least at the distal end of these guide wires, the springs closely surrounding the distal end region and being fastened to it extending over a certain length beyond same. These helical springs are very flexible and are carefully rounded on their outer surface; a securing wire which is laid within the spring and connected to it at both ends prevents the spring from pulling apart so that the helical turns of the spring material lie closely alongside of each other. This helical spring and the distal end of the guide wire are either linear or bent at an angle of up to 180°, radii of curvature of down to 1.5 mm being obtained.

In this way, there is obtained a relatively soft arch on the distal end of the guide wire the legs of which can apply themselves against the channel walls and thus assure elastic guidance of the tip of the guide wire upon its advance into the convoluted canal system without the wall of the canal being pierced by the tip of the guide wire in narrow curvatures. Upon a slight pulling back of the guide wire the helical spring extends and passes from a J-shaped configuration into a merely slightly arched configuration in which the distal end of the helical spring rests against a canal wall. This procedure takes place in the case of narrow branchings which the guide wire is to follow. Special guide wires are designed with torsional stability, as a result of which, for instance, vessel exits can be probed selectively. Because of the high flexibility of the helical spring, the distal end region of the guide wire which is surrounded by the helical spring is preferably tapered or in any event made thinner than the inside diameter of the helical spring. As a result of this, this end region of the guide wire can be slightly bent over, as a result of which the helical spring is, as a whole, imparted the bend necessary for its guidance task and creates a sufficiently large radius of curvature to prevent trauma. For the carrying out of the diagnostic or therapeutic measure within the region of the vasiform lumen, the catheter must then still be pushed over the guide wire and, due to the mechanical properties of the guide wire, its catheter tip can now be selectively positioned.

From Federal Republic of Germany OS No. 33 34 174 a sturdy guide wire of this type is known. It has the disadvantage that, after introduction of the catheter which is pushed over it, it must be removed and replaced by a coaxial catheter in order that a smaller vessel region can be probed or a stenosis passed. The catheter which is introduced in place of the guide wire, however, has only limited mechanical strength with respect to torsional stability and axial load-bearing capacity and it therefore lacks the decisive feature of steerability. Accordingly, it can neither be guided in branches nor pass narrow curvatures and, in particular, it is not possible to pass through stenoses with it. Furthermore, the catheter when introduced, and in particular the position of its mouth, cannot be observed on the fluorescent screen since it does not absorb x-rays.

Catheterlysis treatments by means of a therapeutic agent or laser are also difficult with the known combinations of strong guide wire and catheter because the progress of the treatment can be observed only with difficulty, since, as a result of the single catheter lumen present, the fibrinolytic or x-ray contrast agent must be applied alternately. In particular, the fibrinolytic, which is washed out of the catheter upon each introduction of contrast agent, no longer is active locoregionally in the sense of catheterlysis and thereby systematically subjects the entire organism to stress. In this way, the economy of the use of the fibrinolytic is reduced. Verification of the progress of the thrombolysis therefore naturally takes place in relatively large steps and therefore without sufficient visual control.

From Federal Republic of Germany OS No. 29 16 097 a catheter arrangement having a guide wire is known. In this case, the outer catheter serves as guide catheter for the inner catheter. The guidance character of the guide catheter is based therefore exclusively on its ability to impart external support to the thin and accordingly unstable catheter which is guided in its lumen. It is not possible to go into narrow lumens with this guide catheter, if only because of its necessarily large outside diameter. Its use, therefore, is limited to large-size vessels.

From Federal Republic of Germany AS No. 25 05 790 there is known a hollow puncture needle for use in vein catheter instruments. It is suitable exclusively for manipulations at the place of puncture while the possibility of manipulating the tip of the needle far from the point of puncture is not present.

SUMMARY OF THE INVENTION

Starting herefrom, the object of the present invention is to provide a steerable atraumatic guide wire of the aforementioned type which, upon combined use with the catheter, can be advanced under fluoroscopic control in particularly narrow or constricted lumens of the human or animal body, as for the passing through and-/or probing of small-caliber vessels or extensive vascular stenoses (constrictions) as well as for penetration into closed (for instance, by thrombus or tumor) vessels. Such a guide wire is to be capable of use, in particular, in blood vessels (arteries and veins) and in the gastrointestinal tract (for instance, bile ducts and pancreatic duct) as well as within the efferent urinary tract (for instance, ureter); furthermore, with the use of such a guide wire, smaller vessel regions can be selectively probed or constrictions (stenoses) overcome; in particular, it is desired, with such a guide wire combined with an angiograph catheter pushed over it, to be able to carry out catheterlysis treatments in a thrombus or embolus by targeted administration of streptokinase or urokinase; furthermore, such a guide wire is to be suitable for use for passing through high-degree stenoses or for passage through closures or the overcoming of closure paths caused, for instance by tumors in the bile ducts and in the pancreatic tract with the use of endoscopic techniques; in this connection, the selective probing is to be supported by the possibility of employing x-ray contrast agents, which permits the display of the topographical conditions; finally, such a guide wire should also be capable of use in the angioplasty of constrictions or occlusions of vessels by means of laser.

In order to achieve this goal, a guide wire of the aforementioned type having the features set forth in the body of claim 1 is proposed. In one practical embodiment of the invention, the outside diameter of the metal tube, at least in the distal end region, is about 0.1 to 1.0 mm and preferably 0.2 to 0.5 mm. The invention accordingly is developed on the basic concept of forming a guide wire of the aforementioned type as a continuously hollow, laterally flexible, torsionally stable, non-brittle, axially strong guide tube which is substantially impervious to x-rays and has substantially smooth walls, particularly of metal.

The guide wire of the invention—or rather the guide tube of the invention—has the advantage that fluoroscopically verifiable steerability is combined in it with the property of a catheter. The ability to realize this combination of properties is surprising since the requirements made on a guide wire are opposite those made on a catheter. Despite the small inside diameter of the guide tube, which is between 0.8 and 0.05 mm at least in the distal end region, and despite the considerable length of the guide tube of up to 3 m, it has been found excellently suited for the injection of targeted quantities of therapeutics or contrast agents, as well as for the other treatments described below. Despite its small outside diameter, the guide tube has sufficiently great torsional stability that it can be steered to the required extent in the same way as non-hollow guide wires. By the cylindrically developed distal end region of the metal tube there is obtained a free cross-sectional surface which is sufficiently large for the injection. The helically wound spring which surrounds this distal end region and which consists, in particular, of thin metal wire can be easily bent in the region thereof protruding beyond the end of the mouth of the guide tube so that the desired guidance and steerability are retained even though the distal end region of the guide tube itself remains cylindrical and unbent.

If the distal end of the spring, in accordance with a further development of the invention, has a closure member which is rounded on the outside, the danger of traumas is reduced. Although such a closure member prevents emergence of the injected therapeutic agent at the distal end of the spring, the desired possibility of using the guide tube as catheter is retained since, surprisingly, the flexibility of the spring is sufficient to assure sufficient passage cross sections for the therapeutic agent between the turns of the helix.

A thread, particularly a metal thread, which, in accordance with a further development of the invention, is arranged within the spring and limits the maximum length of the spring and is fastened to both ends of the spring controls the length of the spring in particular in the part extending beyond the guide tube; in this way, the danger of traumas by individual helical turns of the spring is minimized. In one practical embodiment, the spring is metallically connected, in particular soldered, to the end region of the metal tube; in this way, despite the small dimensions of material, high strength and resistance to kinking are obtained while, at the same time, small radii of curvature on the outer surface of the proximal spring end are enlarged. In one practical embodiment, the thread which limits the maximum length of the spring is a wire which is metallically connected to both ends of the spring and is fixed on the proximal end preferably between the outer wall of the guide tube and the inner wall of the helical spring. The end of the spring which protrudes beyond the metal tube forms an arch of between about 30° and 230° and preferably an arch of about 180°, so that the danger of traumas, both upon passage through canals of large cross section and upon passage through very narrow canals is minimized. In this connection, the closure member of the spring should have radii of curvature which are as large as possible.

The handling of the guide tube of the invention both with respect to steerability and with respect to the suitable injection of therapeutics is improved in accordance with another development of the invention by the fact that the metal tube consists of a plurality of tube lengths of different diameter which are inserted one within the other and sealed to each other and that the diameter of what is in each case the distal tube section is smaller than that of the proximal tube section. The diameters and wall thicknesses of the tube sections which are connected to each other are preferably so selected that the tube of smaller outer diameter which is distal in each case can still just be pushed into the proximal tube of larger outside diameter. In this connection the distal end region of the proximal tube can be slightly widened. A sealed connection is produced, for instance, by soldering. A guide tube developed in this manner can have an extremely small outside diameter of down to about 0.1 mm in its distal end region so that even very fine canal branchings and passages can be sought and passed through, since the outside diameter of the metal tube is particularly small and its lateral flexibility in this region is particularly great. On the other hand, the proximal end of the guide tube can have a comparatively large outside diameter of up to 1 or 2 mm and, if necessary, even more, as a result of which the force-locked connection of the guide tube to a turning handle is simplified. Furthermore, with such a guide tube of the decreasing diameter the resistance to flow of the therapeutic agent to be injected decreases as compared with a guide tube which has the same inside diameter over its entire length as it does at the distal end region.

If, in accordance with another development of the invention, the proximal end region of the metal tube is detachably connected to a turning handle which radially surrounds it, then the shape of the turning handle can be adapted particularly well to its task; nevertheless the outside diameter of the proximal end region of the metal tube can be relatively small so that even a very slender catheter can be placed over the metal tube. In principle, the turning handle can, however, also be located in non-detachable manner on the proximal end of the metal tube, for instance in the form of a fluted surface.

An injection adapter which is detachably connected to the proximal end of the metal tube permits injection by means of ordinary syringes. If this injection adapter is detachable, as is preferred, it can be connected also to cannulas which are of large caliber as compared with the guide tube, without the pushing of a catheter thereover being prevented thereby.

If, in accordance with a further preferred embodiment of the invention, a cannula which has a somewhat larger caliber than the guide tube radially surrounds the proximal end region of the metal tube and is connected metallically to it and a turning handle radially surrounds the cannula and can be connected, fixed for rotation, to it and be detached from it then the aforementioned advantages are combined with each other in the best possible manner.

The aforementioned parts used in accordance with the invention are not subject to any special exceptional conditions with respect to their size, shape, selection of material or technical design, so that the criteria for selection known in the specific field of use can be applied without limitation.

Further details, features and advantages of the object of the invention will become evident from the following description of the accompanying drawing, in which preferred embodiments of catheter guide wires according to the invention have been shown.

BRIEF DESCRIPTION OF THE DRAWING

FIG. 1 shows a guide wire with angiograph catheter shown diagrammatically—partially in longitudinal section;

FIG. 2 shows a similar angiograph catheter with guide wire seen in side view with different bends of the spring;

FIG. 3 shows a similar guide wire in longitudinal section—on a greatly enlarged scale shown in different sections;

FIG. 4a shows the guide wire with angiograph catheter according to FIG. 1, introduced into a blood vessel for the catheterlysis of a thrombus;

FIG. 5a shows a guide wire with angiograph catheter according to FIG. 1, introduced into a bile duct in a first operating position, and FIG. 5b shows the same guide wire in a second operating position.

BRIEF DESCRIPTION OF THE PREFERRED EMBODIMENTS

Figure 4B:
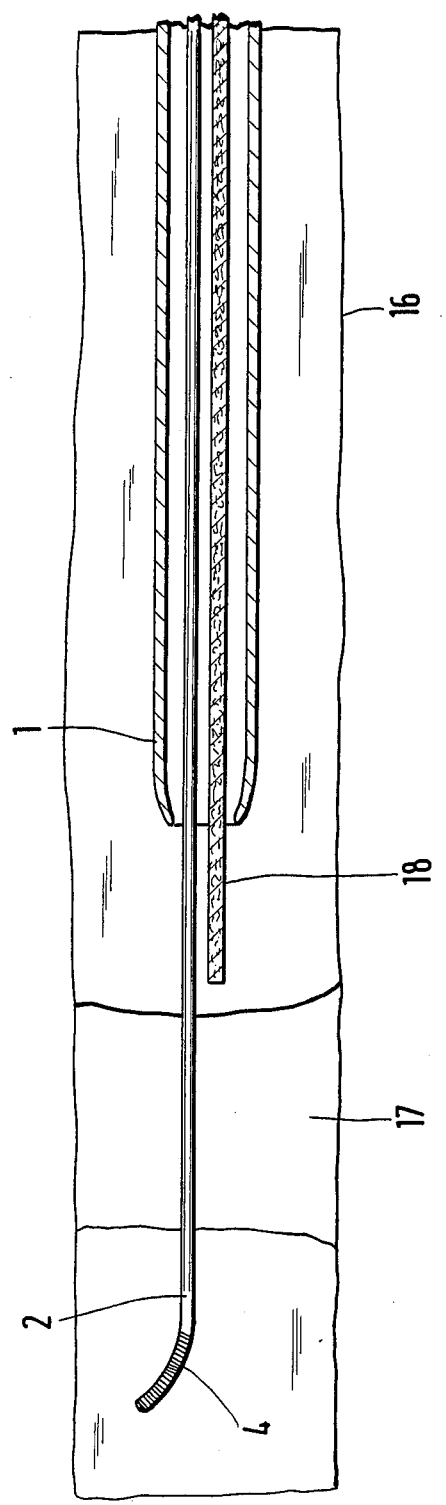
FIG. 4b shows the guide wire with angiograph catheter according to FIG. 1, introduced into an artery for angioplasty by laser.

In accordance with FIG. 1, a steerable, flexible, torsionally-resistant guide wire for medical catheters 1 consists, in accordance with the invention, of a continuous hollow metal tube 2 (guide tube) whose outside diameter is about 0.1 to 1.0 mm and preferably 0.2 to 0.5 mm, at least in its distal end region. At least the distal end region 3 of the guide tube 2 is cylindrical and surrounded by a known helically wound spring 4 which extends beyond the end of the guide tube (Federal Republic of Germany OS No. 33 34 174).

As can be noted in detail from FIG. 3, the guide tube 2 may consist of one or more metal cannulas 7 to 9 connected to each other by solder 5, 6, the outside diameters thereof being preferably less than the outside diameter of ordinary guide wires, i.e. essentially below 1 mm, the outside diameter in particular in the distal end region 3 of the guide tube 2 being preferably between 0.2 and 0.5 mm. The helical spring is preferably a wire helix which is pushed tightly over the distal end region 3 of the guide tube 2 and soldered to it. The undesired drawing-out of this wire helix is prevented by a thread 10, particularly a very fine metal wire, arranged within the spring 4. This safety wire increases the axial tensile strength of the spring and limits its maximum length. The tip of the spring 4 has a closure member 11 which is rounded on the outside and preferably consists of metallic solder material, within which the thread 10 (safety wire) is affixed and thus firmly connected to the end of the spring. The other end of the spring is clamped and preferably soldered fast, between the distal end region 3 of the guide tube 2 and the part of the spring 4 surrounding said end region.

As shown in FIGS. 1 and 3 as well as in the bottom right of FIG. 2 the spring can be bent by about 60° but it can also be bent by about 180° as shown in the top right in FIG. 2. In this way the desired controllability (steerability) is obtained. The radius of curvature and length of the spring 4 are so developed that the 180° J-shaped bend is still just retained in vessels of large inside diameter, for instance the popliteal artery, with slight friction against the wall of the vessel, and can be brought into an axially extended only slightly curved position by slight retraction. As a result of this arrangement, substantially atraumatic passage through atheromatously modified sections of vessels in the manner of a J-guide wire can be assured; on the other hand, the extended tip of the spring, inclined under tension slightly against the wall of the vessel, can be brought selectively into the branchings, for instance of the trifurcation on the lower leg. The rear (proximal) closing of the guide tube 2 is effected via a somewhat larger calibrated cannula 9 which is soldered thereon and on which there is placed a cylindrical turning handle 12 which transmits the torsional force to the guide tube 2 by means, for instance, of a clamp 13 which can be screwed tight. The turning handle can be provided at its rear end with a conical extension—which is known and therefore not specifically shown—for instance, a Luer-lok, for connection with an injection cannula.

The flexible catheter 1, for instance a coaxial angiograph catheter, can be pushed over the guide tube, which has been introduced in customary manner into the vessel to be probed, from the proximal end of said tube. This catheter is preferably shorter than the guide tube and is provided at its proximal end with a so-called Y-connector, through the side arm 15 of which contrast liquid or the like can be introduced, which then emerges at the distal end of the catheter. The seal between the guide tube 2 and the Y-connector 14 is produced by means of an O-ring which is screwed on, for instance in the form of a Tuohy-Borst adapter.

For the attachment of the turning handle connections such as used for instance with the Lunderquist, Owaman or Willson wire are suitable. The stretching of the wire 4 of the guide tube 2 which is necessary for passage through the Y-connector or for introduction into the catheter is effected by means of a cannula with shank which can be displaced axially over the spring and, after the introduction of the guide tube into the blood vessel or the like, returned to the rear end of the guide tube and pulled off there.

One of the possible uses of the guide wire of the invention is catheterlysis, in accordance with FIG. 4a. In this case the guide tube 2 is advanced within a blood vessel 16 up into a thrombus 17 or embolus. The spring 4 can in this connection penetrate into the thrombus.

The administration of streptokinase or urokinase by which the thrombus is dissolved by the minimum required amount of the therapeutic is effected through the guide tube 2. Contrast agent for checking the progress of the lysis is introduced through the angiograph catheter 1. As a result of the advanced position of the tip of the guide tube into the thrombus, the lysis takes place in the most favorable manner without any disturbance caused by contrast agent since the opening of the mouth of the angiograph catheter (contrast-agent catheter) is relatively far proximally in front of the thrombus. Observation of the progress of the lysis is effected in known manner by fluoroscopic control.

In the case of the treatment shown in FIG. 4b, an intravascularly working laser is used with which the angioplasty of constrictions or occlusions of the vessels is possible. One typical problem in this treatment consists in the aligning of the glass fiber 18 which transports the light energy since iatrogenic vascular wall lesions must be avoided. Even the intravascular endoscopic control of the glass fiber cannot prevent lesion to the vascular wall if the vessel bends strongly during the course of the stenosis or occlusion. For the avoidance of iatrogenic lesions on the vascular wall the following procedure is proposed: An angiograph catheter 1 is placed just in front of the stenosis (thrombus 17). Both the guide wire of the invention and the glass fiber 18 are advanced through the angiograph catheter. While the glass fiber 18 scarcely extends beyond the catheter, the guide tube 2 is advanced under fluoroscopic control with addition of contrast agent through the inside of the guide tube over the stenosis or the occlusion path. The definite intraluminal position of the spring 4 distally of the stenosis or occlusion is verified by introduction of contrast agent. The stenosis or occlusion is then lasered with combined advance of glass fiber and catheter. In this connection, the guide tube 2 assumes the guidance of the catheter, which in its turn guides the glass fiber intraluminally. The system permits the use of a single glass fiber. Necessary rinsing away of the blood during the laser application is effected by introduction of contrast agent under fluoroscopic control or by the introduction of rinsing liquid by means of the angiograph catheter 1.

Due to the fact that the guide tube 2 consists of metal, it withstands the thermal stresses upon the laser application. Thus, with the guide wire of the invention it is possible, for the first time, to pass in controlled fashion through high-grade stenoses or occlusion paths while avoiding iatrogenic lesions to the vessel walls. In this way, methods of treatment are possible which previously could be carried out—if at all—only with great risk.

FIG. 5a/b shows how a selective probing of stenoses or the overcoming of, for instance, tumor-caused occlusion paths in the bile ducts and pancreatic duct is possible with the use of endoscopic techniques: By means of the endoscope 19, the guide tube 2 and the angiograph catheter 1 are introduced into the bile duct 20 or pancreatic duct. By the application of contrast agent through the guide tube 2, the duct system can be roentgenolically displayed. As a result of the possibility of controlling the guide tube, fluoroscopically controlled probing is possible. The overcoming of stenosis and occlusion paths is effected in the manner described above. In combination with the guide tube 2 an ordinary thin-walled angiograph catheter 1, for example 5 French, 0.038" lumen, can be introduced. It serves to stabilize the guide tube at the transition from endoscope 19 into the duct system. After passage of the stenosis or occlusion path by the guide tube 2 the catheter 1 can possibly also be pushed over the lesion 21 (see FIG. 5b). In this way, there is the possibility of substituting a more stable rigid guide wire which in its turn assumes the guidance for an endoprosthesis which is to be put into place, if this maneuver cannot be effected alone via the guide tube 2.

I claim:

1. A catheter and wire guide combination comprising
 a wire guide adapted to be independently pushed and steered through blood vessel lumens to a site and comprising a hollow metal tube through which a liquid flows, said tube having a distal end region, a proximal end region and a flexible tubular section of torsional stability, said hollow metal tube having further a mouth opening in said distal end region and an open proximal tube end in said proximal end region,
 a connector for receiving an injection adapter for injecting through the hollow metal tube a first means comprising a liquid directly to the site itself, said connector being connected to the open proximal end of the metal tube,
 a helically wound spring tightly overlappingly surrounding for a substantial support length said distal end region of said metal tube extending beyond said distal end region,
 a turning handle which is connected to the proximal tube end of the hollow metal tube but distally with respect to said connector for said injection adapter and which surrounds the proximal tube end coaxially and only radially,
 a hollow flexible catheter being freely coaxially pushable over said wire guide independently of the position of said wire guide for being moveable in said blood vessel lumens directly to the site, said catheter having open proximal and distal ends,
 a Y-connector connected to the proximal end of the catheter and having a hollow side arm communicating with the open proximal end for pushing a second means comprising a liquid therethrough directly to the site itself independently of liquid passing through the hollow metal tube, whereby two liquids simultaneously can be passed through said catheter and said metal tube to the site,
 said Y-connector being adapted for receiving said hollow metal tube in a fluid tight manner with respect to said second means,
 said wire guide being freely relatively moveable lengthwise and rotatably with respect to said Y-connector and to said hollow flexible catheter.

2. The combination according to claim 1, wherein the metal tube comprises a plurality of tube sections of different diameter which each of said tube sections, having proximal and distal end regions, said tube sections are inserted one within the other so that only the end regions of neighboured tube sections overlap each other and are sealed to each other and that the diameter of each distal tube section is smaller than that of each proximal tube section.

3. The combination according to claim 1, wherein the hollow metal tube has a constant caliber throughout.

4. The combination according to claim 1, further comprising a cannula with a proximal and distal end which at least with its distal end radially surrounds the proximal tube end of the hollow metal tube and is metallically connected to it, and said turning handle radially surrounds the cannula and is connected fixed for rotation thereto, and said cannula protrudes from said handle and receives said connector for said injection adapter at its proximal end.

5. The combination according to claim 4, wherein the turning handle is detachable from the proximal tube end of the hollow metal tube.

6. The combination according to claim 4, wherein the connector for the injection adapter is detachable from the proximal tube end of the hollow metal tube.

7. The combination according to claim 1, wherein the turning handle is detachable from the proximal tube end of the hollow metal tube.

8. The combination according to claim 7, wherein the connector for the injection adapter is detachable from the proximal tube end of the hollow metal tube.

9. The combination according to claim 1, wherein the connector for the injection adapter is detachable from the proximal tube end of the hollow metal tube.

* * * * *